United States Patent [19]

Gannon

[11] Patent Number: 4,756,140
[45] Date of Patent: Jul. 12, 1988

[54] VACUUM PACKAGING PROCESS

[75] Inventor: Raymond Gannon, London, United Kingdom

[73] Assignee: FGL Projects Limited, London, England

[21] Appl. No.: 925,893

[22] Filed: Oct. 31, 1986

[30] Foreign Application Priority Data

Nov. 2, 1985 [GB] United Kingdom ............. 8527050

[51] Int. Cl.⁴ .................... B65B 31/02; B65B 31/04
[52] U.S. Cl. .......................... 53/434; 53/373; 53/408; 53/512
[58] Field of Search .............. 53/432, 434, 403, 408, 53/512, 373, 427

[56] References Cited

U.S. PATENT DOCUMENTS

| | | |
|---|---|---|
| 3,630,665 | 12/1971 | Anderson et al. ............. 53/434 |
| 3,965,653 | 6/1976 | Lerner ........................... 53/373 |
| 3,980,226 | 9/1976 | Franz ............................. 53/434 |
| 4,457,122 | 7/1984 | Atkins et al. .................. 53/434 |
| 4,541,224 | 9/1985 | Mugnai .......................... 53/512 |
| 4,545,177 | 10/1985 | Day ................................ 53/434 |

FOREIGN PATENT DOCUMENTS 2708444 8/1978 Fed. Rep. of Germany ........ 53/434
2107270 4/1983 United Kingdom ................. 53/434

Primary Examiner—Robert L. Spruill
Assistant Examiner—Donald R. Studebaker
Attorney, Agent, or Firm—Henry Sternberg; Bert J. Lewen

[57] ABSTRACT

A process of packaging goods, especially foodstuffs, comprising enclosing the goods in a sheet of thermoplastics material, preferably a bag, so as to form a package which presents two unsealed juxtaposed surfaces. The package is then placed in a container, one wall of which is made of deformable sheet material, preferably a sheet made of a silicone resin, which is stable at the sealing temperature of the thermoplastics material. The container is then connected to a source of vacuum and when the pressure has been reduced in both the container and the bag sufficient heat is applied to the deformable sheet in the vicinity of the juxtaposed surfaces to cause them to become sealed together. In a further embodiment of the invention vacuumization of the container including the bag is followed by the injection of a preserving gas such as carbon dioxide.

19 Claims, 2 Drawing Sheets

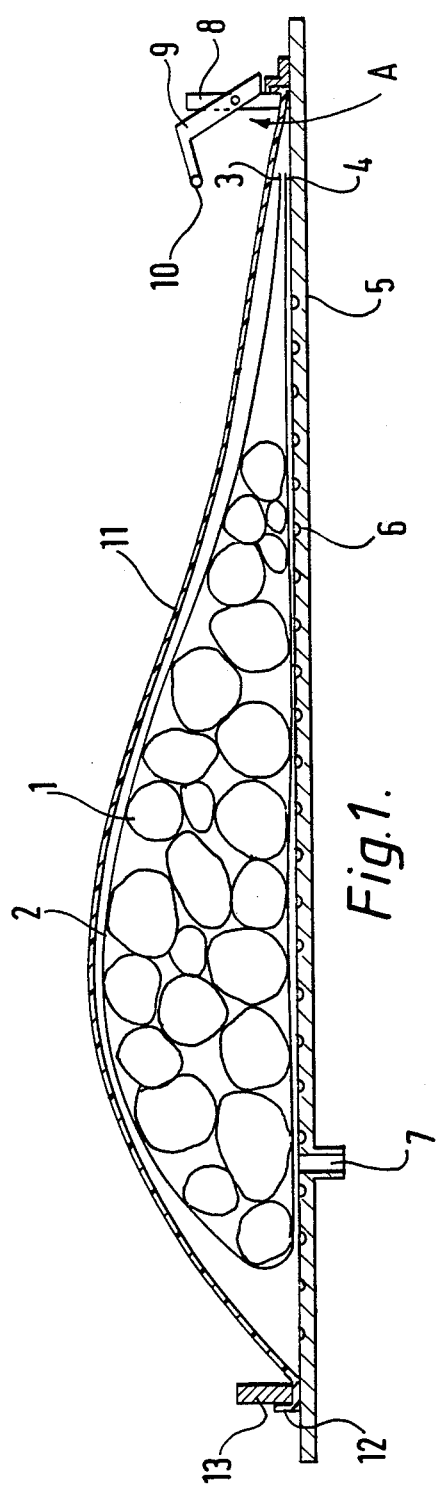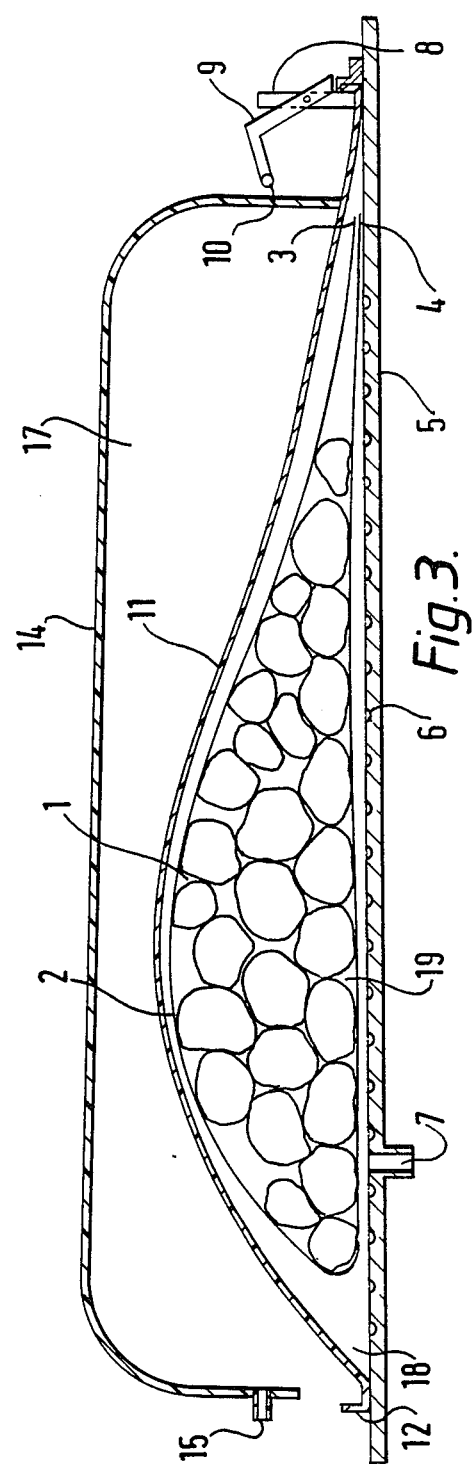

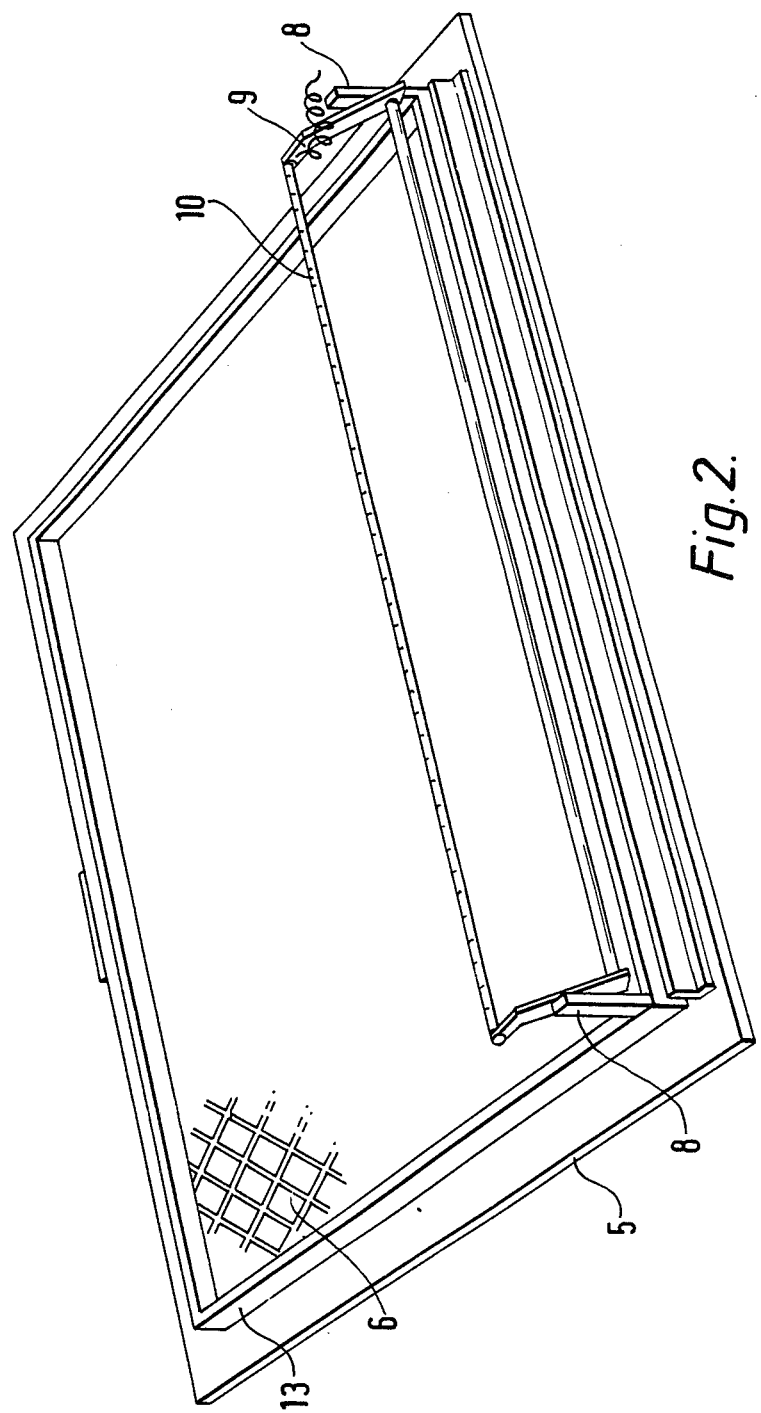

VACUUM PACKAGING PROCESS

This invention relates to an improved vacuum packaging process. Vacuum packaging of goods, that is to say the packing of goods in containers having gas impermeable walls and from which air has been removed or replaced by gases having a preserving effect, is becoming of increasing importance as a means of enabling foodstuffs to retain for longer periods much of their original freshness without relying to the same extent on conventional preservatives. The process is also being extended to a large variety of other goods, for example the packaging of electrical and electronic components, medical samples and instruments.

One of the processes which is used widely involves placing the goods in unsealed containers, for example bags made of thermoplastics material such as polyethylene, and then placing the containers in a larger chamber having square or other rectangular shaped walls provided with an air-tight lid. The chamber is then connected to a source of vacuum and when the vacuum of the desired extent has been created in the chamber the individual containers are then sealed before they are removed. This process whilst giving a measure of success has nevertheless some important disadvantages. Thus the need to seal the packages whilst they are still in the chamber results in considerable amount of dead space being created, i.e. space which is not occupied by packages which are required to be vacuumized. Consequently not only is there a wastage of space but in addition the vacuumizing process is prolonged because until the air in the dead space has been pumped out the desired degree of vacuum within the individual bags cannot be achieved. A further disadvantage is that the equipment necessary for carrying out the process is fairly complicated and therefore expensive. The present invention enables vacuumizing equipment to be made more cheaply and permits the process to be carried out more rapidly and is more versatile in its operation.

Accordingly this invention provides a process of packaging goods comprising enclosing the goods in a sheet of thermoplastics material so that the resulting package presents two unsealed juxtaposed surfaces of the sheet material, placing the package in a container of which one wall is provided by a deformable sheet of material stable at the sealing temperature of the thermoplastics material, connecting the container to a source of vacuum and applying sufficient heat to the deformable sheet material in the vicinity of the juxtaposed surfaces of the thermoplastics sheets to cause the sheets to become sealed together.

The term 'stable' used in this specification is taken to mean that the deformable sheet in relation to which the term is used shall retain its integrity under conditions of use. Thus if the sheet is made of fusible material it must have a melting point which is substantially higher than that of the material forming the bag.

This invention is illustrated but not restricted by the following drawings in which:

FIG. 1 shows a side view taken in vertical section of one form of an apparatus for carrying out a process according to the present invention.

FIG. 2 shows in perspective a heat sealing device which is shown generally as A in FIG. 1.

FIG. 3 shows a view taken in vertical section of an alternative form of apparatus for carrying out the process.

In FIG. 1 the goods (1) are placed in a bag (2) made of a sheet of polyethylene which is a thermoplastics material. Opposing lips (3 and 4) of the bag are unsealed with one lip resting on the other. The unsealed bag (2) is placed on a sealing base (5) the upper surface of which is provided with numerous inter-communicating channels arranged in a cross hatch pattern (6) and an apertured member (7) for connection to a source of vacuum (not shown). The base is also provided with a heat sealer consisting of an upright (8) to which arm (9) is connected pivotally. The arm terminates in sealing head (10) heated electrically by means not shown. Bag (2) is covered with a flexible sheet (11) made from a sheet of stable heat resistant silicone resin the edges of which (12) are pressed into air-tight engagement with sealing base (5) by frame (13) connected by a hinge to base (5).

FIG. 2 shows more clearly the construction of the sealing apparatus.

In operation when the goods in the bag have been placed on sealing base (5) the sheet of silicone material is draped over the bag and the edges secured to sealing base (5) by lowering the frame and fixing it in a closed position with the edges of the silicone sheet pinched between the frame and the base (5). A source of vacuum is then connected to aperture (7) and as the pressure is reduced in the space between sheet (11) and base (5) the sheet clamps down and compresses the bag (2) causing air to be expelled from the bag between two edge portions (3 and 4). When the desired degree of vacuum has been achieved arm (8) of the heat sealer is rotated in an anti-clockwise direction until head (10) touches the sheet. At the same time as arm (8) commences to move a switch is actuated causing current to heat the head (10). Sufficient heat is transmitted by the sheet to seal the lips (3 and 4) of the bag together. The vacuum can then be disconnected, the frame raised thus releasing the silicone sheet and the bag.

During the vacuumizing process extraction of air from the space between the sheet and the base and hence from the bag itself is facilitated by the cross hatch of channelling (6). There are nevertheless certain goods from which sufficient air cannot be abstracted very readily because of the rapid compression of the goods which takes place and which prevents the air having sufficient opportunity to escape. In such cases the vacuumization of the goods is carried out preferably prior to any substantial compression of the product is permitted to take place. This can be achieved utilising the apparatus described in FIG. 3. The same numerals shown in FIGS. 1–3 represent the same features. In FIG. 3 frame (13) of the previous two figures is replaced by a dome (14) or cover having a rigid wall and made conveniently of stainless steel or of a transparent material for example a polycarbonate plastics. The dome is provided with an inlet (15) and is connected hingedly to sealing base (5).

In operation dome (14) is swung upwards and backwards on its hinges and the goods (1) contained in a bag made of polyethylene plastics is placed on sealing base (5) and covered with a stable silicone sheet (11). The dome is then pivotted to a closed position with the rim of the dome pressing tightly on the exposed edges of the silicone sheet so as to form an air-tight seal. The interior of the dome is now divided effectively into three separate spaces shown generally as numerals 17, 18 and 19. Space 17 is that defined by dome (14) and silicone sheet (11). The second is between the silicone sheet and sealing base (5) whilst the third is formed by the interior of the bag (2). Inlets (7 and 15) are then connected to a source of vacuum and by balancing the rate of extraction of air through both inlets the pressure in all three spaces can be reduced simultaneously and to the same extent with the result that the pressure in the bag can be reduced without any compression of the contents taking place. Under such circumstances air trapped in the goods can escape freely between lips (3 and 4) of bag (2). When the pressure in all three spaces has been reduced to the desired extent air is admitted into space (17) through inlet (15) which conveniently can be provided with a three way valve one channel communicating with the source of vacuum, the second with space (17) and the third communicating with the outside atmosphere. When air enters space (17) sheet (11) is forced by atmospheric pressure onto bag (2) compressing the contents. When no further compression takes place the dome is removed and the bag is then sealed with sealing mechanism (8, 9 and 10) in the manner described above.

In general when a bag is employed the mouth of the bag is left completely open until the sealing operation is to be carried out. However in certain instances the bag can conveniently be partly sealed before it is inserted into the container or alternatively a bag can be used which incorporates a valve incorporating thermoplasatics material. When a valve is used the mouth of the bag can be sealed completely outside of the container and the bag placed in the container with the valve in the open condition. When the vacuumizing process has been carried out the valve can then be closed with the sealer by causing juxtaposed surfaces of material forming the valve to become fused together.

The present process is of special value in the preservation of goods with certain gases known to have a preserving action, for example carbon dioxide, nitrogen, nitrous oxide and oxygen. These gases can be used singly or as mixtures depending upon the nature of the goods to be packaged. For many purposes carbon dioxide used on its own has been found to give very good results although a mixture of from 14 to 40% by volume of carbon dioxide, 5 to 28% of nitrogen and 8 to 20% of oxygen is often very satisfactory.

The method of using a preserving gas depends upon the form of equipment to be employed for vacuumizing the package. Thus in the case of the aparatus described in FIGS. 1 and 2 the vacuumizing process is carried out in the manner described except that prior to sealing of the bag the preserving gas is admitted through inlet (7) which conveniently can be provided with a three way valve, one channel communicating with the source of vacuum, a second channel communicating with the source of preserving gas and the third with the interior of the apparatus. When the gas has been admitted the bag is then sealed in the usual way.

The sequence of steps to be followed with the apparatus described in FIG. 3 is similar except that the gas is admitted through inlet (7) whilst a vacuum exists in all three spaces. As a consequence the bag re-inflates. When this has taken place space (17) is brought to atmospheric pressure by opening the valve (not shown) on inlet (15). The bag can then be sealed in the normal way.

The apparatus used for carrying out the process of the invention can be varied in a number of other ways. For example the sealing plate can be made of any conventional construction material, for examples plastics, wood or metal. It can be rigid or flexible and for certain purposes it can even be made of a heat resistant sheet of plastics material, for example a silicone resin. The sealing base can be solid except for the presence of any channelling or it can take the form of a tray over the top of which can be stretched a heat resistant gas permeable fabric made from silicone or coated nylon threads.

The frame can be detachably secured to the sealing plate and it can be replaced by a frame of different size or shape, e.g. an oval shape. In the illustration bags have been employed to package the goods. However, an alternative procedure is to place the goods on a flat sheet of thermoplastics material, covering the goods with a separate sheet and then forming an airtight seal with the sealing base, the silicone sheet and according to the nature of the goods to be packaged the frame or the rim of the dome. In this application, heat for sealing purposes would have to be applied to the whole periphery of the package and this can be achieved conveniently with a jet of hot air.

Any convenient form of vacuum pump can be employed to vacuumize the packages. However a very satisfactory device is the subject of our copending European Patent Publication No. 0210765, published Feb. 4, 1987, which is directed to a combination of a by-pass fan pump, a conduit connecting the pump to an applicator head and means enabling a part of a stream of air entering the pump to bypass the applicator head. A venturi pump can constitute the by-pass means.

The deformable sheet of stable material can have either a smooth surface or preferably the surface facing the package can be embossed or otherwise provided with protuberances which define a pattern of channels. By this means when pressure is reduced between the sheet and the package the deformable sheet is unable to make continuous contact with the outer surface of the package and as a consequence a greater area of the package is exposed to the reduction in pressure. This in turn enables air to be discharged more satisfactorily from the package.

What is claimed is:

1. A process of packaging goods, which comprises providing the goods, enclosed in packaging sheeting of thermoplastic material to form a heat sealable package, in an evacuatable container having one wall portion thereof formed of a deformable sheet of heatable material stable at the sealing temperature of the thermoplastic material, so that the resulting package presents two unsealed juxtaposed surfaces of the packaging sheeting adjacent a portion of the deformable sheet, evacuating the container to remove attendant air from the package through said unsealed juxtaposed surfaces, and heating locally said portion of the deformable sheet in the vicinity of said juxtaposed surfaces to transmit sufficient heat through the deformable sheet thereat to cause the juxtaposed surfaces to become sealed together.

2. Process of claim 1 wherein a preserving gas is introduced into the evacuated container and in turn through said unsealed juxtaposed surfaces into the package, prior to said heating.

3. Process of claim 2 wherein the gas is at least one of carbon dioxide, nitrogen, nitrous oxide and oxygen.

4. Process of claim 1 wherein said juxtaposed surfaces of said portion of the deformable sheet are locally physically squeezed together during said heating.

5. Process of claim 4 wherein the container has another wall portion thereof formed as a base, the package is located on the base such that said juxtaposed surfaces are disposed between said portion of the deformable sheet and the base, and the heating is carried out by means of a heating member movable to squeeze said portion of the deformable sheet and said juxtaposed surfaces against the base during the heating.

6. Process of claim 1 wherein the package is in the form of a bag having an opening defined by said unsealed juxtaposed surfaces.

7. Process of claim 6 wherein the bag has a sealed mouth through which the bag has been prefilled with the goods prior to sealing the mouth, and the bag further has an open valve of said thermoplastic material which forms the opening defined by said juxtaposed surfaces.

8. Process of claim 1 wherein the package is in the form of a pair of separate superimposed sheets of said thermoplastic material enclosing the goods and having a composite periphery providing said two unsealed juxtaposed surfaces, and said periphery is adjacent said portion of the deformable sheet.

9. Process of claim 1 wherein the container has another wall portion thereof formed as a base provided with a plurality of interconnecting channels, and the package is located on the base in facing communication with the channels to facilitate removal of attendant air during the evacuating.

10. Process of claim 1 wherein the deformable sheet is arranged to divide the interior of the container into a first pressure space and a second pressure space, the package is provided in the second space, and the evacuating is carried out without initial compression of the goods in the package by simultaneously reducing the air pressure in both spaces, and thereafter raising the air pressure only in the first space to force the deformable sheet against the evacuated package in the second space.

11. Process of claim 10 wherein after reducing the air pressure in both spaces, a preserving gas is introduced into the evacuated second space and in turn into the package through said unsealed juxtaposed surfaces, prior to raising the air pressure only in the first space.

12. Process of claim 11 wherein the gas is at least one of carbon dioxide, nitrogen, nitrous oxide and oxygen.

13. Apparatus for packaging goods in packaging sheeting of thermoplastic material having two unsealed juxtaposed surfaces to be heat sealed together, which comprises an evacuatable container having one wall portion thereof formed of a deformable sheet of heatable material stable at the sealing temperature of the thermoplastic material of the resulting goods filled package, and another wall portion thereof formed as a base, the deformable sheet and base being separate from each other and disposed in operative facing relation for relative movement from an open spaced apart position to a closed position in contact with each other to define a closed space therebetween for locating the package on the base with two unsealed juxtaposed surfaces of the package adjacent a portion of the deformable sheet, outlet means arranged for connecting the closed space to a source of vacuum for evacuating the space, and heating means arranged for locally heating said portion of the deformable sheet when the package is in the closed space for transmitting sufficient heat through the deformable sheet thereat to cause the unsealed juxtaposed surfaces of the package to become sealed together.

14. Apparatus of claim 13 wherein the base is provided with a plurality of interconnecting channels arranged for facing communication with the adjacent portion of the package locatable on the base.

15. Apparatus of claim 13 wherein the outlet means are arranged for alternately connecting the closed space to a supply of preserving gas.

16. Apparatus of claim 13 wherein the heating means includes a heating member movable to squeeze said portion of the deformable sheet and the juxtaposed surfaces of the package against the base during the heating.

17. Apparatus of claim 13 wherein the deformable sheet is movable toward and away from the base, and in the closed position is maintained in air tight engagement with the base by means of a movable frame arranged for urging the deformable sheet against the base.

18. Apparatus of claim 17 wherein the frame constitutes the rim of a movable cover having a rigid wall which, when the frame is urged against the deformable sheet, defines a further closed space with the side of the deformable sheet remote from the first mentioned closed space defined between the deformable sheet and the base, and further outlet means are provided for connecting said further closed space to a source of vacuum for evacuating the further space.

19. Apparatus of claim 18 wherein the further outlet means are arranged for alternately connecting the further closed space to a source of air pressure, and the first mentioned outlet means are arranged for alternately connecting the first mentioned closed space to a supply of preserving gas.

* * * * *